United States Patent [19]

Kulcsar et al.

[11] 4,404,189

[45] Sep. 13, 1983

[54] SYNERGISTIC ANTIMICROBIAL COMPOSITIONS

[75] Inventors: Gábor Kulcsár; Gyula Sebestyén; Ágoston Dávid; Tibor Zilahi, all of Budapest, Hungary

[73] Assignee: Chinoin Gyogyszer Es Vegyeszeti Termekek Gyara Rt., Budapest, Hungary

[21] Appl. No.: 226,615

[22] Filed: Jan. 21, 1981

[51] Int. Cl.$^3$ .............................................. A61K 35/00
[52] U.S. Cl. .................................................... 424/114
[58] Field of Search ........................................ 424/114

[56] References Cited

U.S. PATENT DOCUMENTS 3,907,771  9/1975  Weinstein et al. ................... 424/180
3,949,077  4/1976  Buzna et al. .......................... 424/114

FOREIGN PATENT DOCUMENTS 7618799  6/1976  France ................................. 424/180

*Primary Examiner*—Jerome D. Goldberg
*Attorney, Agent, or Firm*—Karl F. Ross; Herbert Dubno

[57] ABSTRACT

A synergistic antimicrobial active ingredient for a pharmaceutical or veterinary composition comprises 5 to 50 percent by weight of a primycin component which consists of a primycin fermentation product of *Thermonospora galeriensis* and 95 to 50 percent by weight of at least one other component selected from the group which consists of doxycyline compounds and sisomicin compounds. The doxycycline compounds are selected from the group which consists of doxycycline, salts thereof with mineral acids, and doxycycline tryclate. The sisomicin compounds are selected from the group which consists of sisomicin, substituted sisomicins with substitution at the N atom by lower alkyl, hydroxyl lower alkyl, lower aminoalkyl and lower alkanoyl, and sisomicin acid salts.

2 Claims, No Drawings

SYNERGISTIC ANTIMICROBIAL COMPOSITIONS

The present invention relates to new synergistic antimicrobial compositions.

The resistance of pathogens to commercially available active ingredients has increased to a great extent and thus several long-used effective active ingredients cannot be effectively used any longer.

In addition to the cromosomal resistance the recently discovered "plasmid resistance" is responsible for the resistance phenomenon. The latter is the capability of pathogens to directly transfer the plasmid resistance thereof to individuals belonging to the same species or other species as well. Thus polyresistant pathogens may be produced within a short period.

Due to the above facts the use of active ingredient combinations is becoming more important. The interaction of simultaneously administered active ingredients—antagonism, synergism—has been known for a long time. Synergism means an increased effect of the combinations related to the components, and this effect is especially important in case of mixed infections.

The present invention deals with synergistic antimicrobial pharmaceutical compositions which comprise 5 to 50 percent by weight of primycin or a derivative thereof and 95 to 50 percent by weight of doxycycline or a derivative thereof and/or sisomicin or a derivative thereof. The composition can include inert solid or liquid non-toxic pharmaceutically acceptable carriers. The mixture can be formulated into a pharmaceutical composition or dosage form.

The synergistic pharmaceutical compositions according to the invention have the following advantages:

1. By attacking the metabolism of the pathogens simultaneously at several points a "cidal" effect can be better achieved and this effect is more advantageous than the "static" effect which is a simple inhibition of the development of the microorganisms.

2. In case of an attack upon several metabolism routes the resistance against the used active ingredient combination does not occur at all or occurs only after a long time.

3. As a consequence of the synergistic effect between the active components, the amount of the active ingredients used can be reduced to a great extent, having the following advantages:

(a) In case of a long-lasting administration the toxicity of the components is greatly reduced by reducing the effective amounts introduced to the organism.

(b) In case of some more expensive compositions the reduced active ingredient amounts may have economic advantage as well.

As further advantage one may mention that in case of some active ingredient combinations not only the extent of the minimal inhibitory concentrations decreases significantly, but in most of the cases the spectrum of activity is also broader.

We have now found that primycin and its derivatives prepared from *Thermomonospora galeriensis* strain by fermentation (HU-PS No. 153 593) in an amount of 5 to 50% by weight gives a synergistic effect with 95 to 50% by weight of sisomicin and/or doxycycline.

Due to the strong synergistic effect the combinations according to the invention are effective and have a broad spectrum of activity and thus may be successfully employed against polyresistant strong pathogen microorganisms capable of causing severe epidemics and diseases. The composition is particularly favorable in the case of mixed infections.

Compositions according to the invention may preferably contain primycin in the form of heterocolloidal primycin (GB-PS No. 1 512 604).

Compositions according to the invention contain as doxycycline derivative a doxycycline salt of a mineral acid, preferably doxycyclic-hydrochloride or doxycycline-hyclate.

As a sisomicin derivative the compositions according to the invention may contain sisomicin substituted on the nitrogen atom by lower alkyl, hydroxy-lower alkyl, lower aminoalkyl or lower alkanoyl or a sisomicin salt of an acid. As sisomicin derivatives preferably N-methyl, N-hydroxyethyl, N-acetyl-sisomicin or sisomicin-hydrochloride may be employed.

Doxycycline and its derivative mentioned above (GB-PS No. 845 649) and sisomicin and derivatives thereof mentioned above (U.S. Pat. No. 3,907,771 and HU-PS No. 170 513) are known compounds.

According to one preferred embodiment of the present invention as active ingredient primycin and sisomicin are used. According to another feature of the invention as active ingredients primycin and doxycycline are used. In the above combinations the derivatives of said antibiotics mentioned above may be employed as well.

A preferred composition according to the invention contains 30 to 35% primycin, 30 to 35% doxycycline or an equivalent amount of the hydrochloride thereto and 30 to 35% by weight of sisomicin related to the total active ingredient content.

The synergistic pharmaceutical compositions according to the invention may be formulated in solid forms such as tablets, capsules, dragées, suppositories, semi-solid forms such as ointments, or liquid forms such as injectable solutions, suspensions or emulsions. As the most advantageous formulations gels, ointments, talcs, injectable solutions or suspensions, and powder-ampoule-solvent-ampoule combinations may be mentioned. The compositions may be administered orally, parenterally rectally or topically, e.g., as ointments.

The pharmaceutical compositions may contain pharmaceutically acceptable carriers, such as magnesium carbonate, magnesium stearate, starch, talc, water etc. and optionally excipients, e.g. fillers, disintegrating agents, lubricants, emulsifiers etc.

Orally administered compositions may be in form of tablets, capsules or dragées.

The synergistic compositions may be employed in the veterinary therapy too, for example as a powder mixture mixed to the feed or as a solution mixed to the watering mixture of the animals.

The parenterally employed compositions may be in form of aqueous solutions, emulsions or suspensions. For topical use one may employ ointments, aqueous or oily emulsions or suspensions or sprays. A parenterally employable composition may be prepared by filling sisomicin and doxycycline into powder ampoules in the presence of sodium acetate, and into solvent ampoules heterocolloidal primycin and surfactants, preferably quaternary ammonium salts such as cetyl trimethylammonium bromide are placed. The content of the solvent ampoule is injected into the powder ampoule directly prior to use. After dissolving an effective veterinary injectable composition is obtained.

A parenterally administrable composition may preferably be prepared by admixing the aqueous alcoholic solution of primycin with a suitable carrier (e.g. castor-oil) and by suspending sisomicin and/or doxycycline in the castor-oil mixture obtained after distilling off alcohol and after cooling.

The ointments may be prepared by distributing the active ingredient components homogeneously in a conventionally used ointment e.g. vaseline.

The biological (in vitro) activity of the compositions according to the invention is demonstrated in the following Examples.

The following international resistant and/or polyresistant human pathogen and/or animal pathogen microorganisms were used in the course of the tests:
1. *Vibrio parahaemolyticus* CCM. 5938,
2. *Pseudomonas acidovorans* CCM. 283,
3. *Proteus vulgaris* CCM. 1799,
4. *Proteus mirabilic* CCM. 1944,
5. *Shigella sonnei* CCM. 1373,
6. *Salmonella typhimurim* CCM. 5445,
7. *Salmonella cholerae-suis* CCM. 5438, (Inst. Pasteur Stamm),
8. *Salmonella cholerae-suis* CCM. 5874,
9. *Salmonella cholerae-suis* subsp. Kunzendorf. CCM. 5967.
10. *Escherichia coli* DSM. 30038,
11. *Escheichia coli* ATTC 11775, cyctitis, poultry pathogen,
12. *Escherichia coli* CCM. 180, lysogenicus, colicinogenicus,
13. *Escherichia coli,* CCM. 5863, haemolyticus,
14. *Klebsiella pneumoniae* CCM. 1848,
15. *Serratia Macerscens* CCM. 303,
16. *Staphylococcus aureus* CCM. 885,
17. *Staphylococcus aureus* DSM. 20231,
18. *Staphylococcus aureus* CCM. 2317, human mastitis,
19. *Staphylococcus aureus* CCM. 2326 human mastitis,
20. *Staphylococcus aureus* CCM. 2515 beta haemylysis,
21. *Staphylococcus aureus* CCM. 2515 coagulase positive,
22. *Streptococcus faecalis* CCM. 885,
23. *Streptococcus agalactiae* CCM. 5153, from cow milk of cows having mastitis,
24. *Streptococcus agalactiae* CCM. 5534, from cow milk of cows having mastitis,
25. *Bacillus cereus* CCM. 2010,
26. *Listeria monocytogenws* CCM. 5576.

ATCC = The American Type Culture Collection,
CCM = Czechoslovak Collection of Microorganisms,
DSM = Deutsche Sammlung für Mikroorganismen.

Abbreviations:
P = primycin sulphate
S = sisomicin sulphate
D = doxycycline sulphate
μg./ml. = microgramm/milliliter
MIC = minimal inhibitory concentration
O = no growth, complete inhibition of the microorganism
± = poor growth
+ + = moderate growth
+ + + = strong growth, no inhibition The tests were carried out on DIFCO Bouillon medium, evaluation after incubation for 24 and 48 hours resp. at 37° C.

Table I to XIII show that the combinations of primycin-prepared from the ferment broth of *Thermomonospora glariensis*—with sisomicin or doxycycline have a synergistic effect and the potentiating effect may increase the original activity by 30 to 40 times.

The pharmaceutical compositions according to the invention may contain other active ingredients such as chemotherapeutic agents as well.

TABLE I

| Primycin + Sisomicin | | | | | | | | | | | |
|---|---|---|---|---|---|---|---|---|---|---|---|
| *Staphylococcus aureus* CCM. 2317. | | | | *Staphylococcus aureus* CCM. 2326. | | | | *Staphylococcus aureus* CCM. 2514. | | | |
| P μg/ml | S μg/ml | Incubation | | P μg/ml | S μg/ml | Incubation | | P μg/ml | S μg/ml | Incubation | |
| | | $24^h$ | $48^h$ | | | $24^h$ | $48^h$ | | | $24^h$ | $48^h$ |
| 0.1 | 0.1 | 0 | 0 | 0.5 | 0.5 | 0 | 0 | 0.5 | 0.5 | 0 | 0 |
| 0:0.75 | 0.1 | 0 | 0 | 0.25 | 0.25 | 0 | 0 | 0.25 | 0.25 | 0 | 0 |
| 0.075 | 0.075 | 0 | 0 | 0.1 | 0.25 | 0 | 0 | 0.1 | 0.25 | 0 | 0 |
| 0.05 | 0.1 | 0 | 0 | 0.075 | 0.25 | 0 | 0 | 0.075 | 0.25 | 0 | 0 |
| 0.05 | 0.075 | 0 | 0 | 0.1 | 0.1 | 0 | +++ | 0.1 | 0.1 | 0 | +++ |
| 0.025 | 0.075 | 0 | 0 | 0.1 | 0.075 | 0 | +++ | 0.1 | 0.075 | 0 | +++ |
| 0.05 | 0.05 | 0 | + | 0.075 | 0.1 | 0 | +++ | 0.075 | 0.1 | 0 | +++ |
| 0.025 | 0.05 | 0 | + | 0.075 | 0.075 | 0 | +++ | 0.075 | 0.075 | + | +++ |
| 0.025 | 0.025 | +++ | +++ | 0.05 | 0.01 | +++ | +++ | 0.05 | 0.01 | +++ | +++ |
| 0.01 | 0.01 | +++ | +++ | 0.05 | 0.075 | 0 | +++ | 0.05 | 0.075 | +++ | +++ |
| Control | | +++ | +++ | Control | | +++ | +++ | Control | | +++ | +++ |
| MIC: P = 0.25, S = 0.25 | | | | MIC: P = 0.5, S = 0.5 | | | | MIC: P = 0.5, S = 0.5 | | | |

TABLE II

| Primycin + Sisomicin | | | | | | | | | | | |
|---|---|---|---|---|---|---|---|---|---|---|---|
| *Staphylococcus aureus* DSM. 20231. | | | | *Streptococcus faecalis* CCM. 1875. | | | | *Streptococcus agalactiae* CCM. 5534. | | | |
| P μg/ml | S μg/ml | Incubation | | P μg/ml | S μg/ml | Incubation | | P μg/ml | S μg/ml | Incubation | |
| | | $24^h$ | $48^h$ | | | $24^h$ | $48^h$ | | | $24^h$ | $48^h$ |
| 0.5 | 0.5 | 0 | 0 | 1 | 2.5 | 0 | 0 | 0.5 | 2.5 | 0 | 0 |
| 0.25 | 0.25 | 0 | 0 | 0.75 | 1 | 0 | 0 | 0.25 | 1 | 0 | 0 |
| 0.1 | 0.25 | 0 | 0 | 0.75 | 0.75 | 0 | 0 | 0.25 | 0.75 | 0 | 0 |
| 0.075 | 0.25 | 0 | 0 | 0.5 | 1 | 0 | 0 | 0.1 | 1 | 0 | 0 |
| 0.1 | 0.1 | 0 | +++ | 0.5 | 0.75 | 0 | 0 | 0.1 | 0.75 | 0 | 0 |
| 0.1 | 0.075 | 0 | +++ | 0.5 | 0.5 | 0 | 0 | 0.25 | 0.5 | 0 | +++ |
| 0.075 | 0.1 | 0 | +++ | 0.25 | 1 | 0 | 0 | 0.1 | 0.5 | + | +++ |

TABLE II-continued

| Primycin + Sisomicin | | | | | | | | | | | |
|---|---|---|---|---|---|---|---|---|---|---|---|
| *Staphylococcus aureus* DSM. 20231. | | | | *Streptococcus faecalis* CCM. 1875. | | | | *Streptococcus agalactiae* CCM. 5534. | | | |
| P | S | Incubation | | P | S | Incubation | | P | S | Incubation | |
| µg/ml | µg/ml | $24^h$ | $48^h$ | µg/ml | µg/ml | $24^h$ | $48^h$ | µg/ml | µg/ml | $24^h$ | $48^h$ |
| 0.075 | 0.075 | 0 | +++ | 0.25 | 0.75 | 0 | +++ | 0.1 | 0.25 | +++ | +++ |
| 0.05 | 0.01 | +++ | +++ | 0.25 | 0.5 | +++ | +++ | 0.1 | 0.1 | +++ | +++ |
| 0.05 | 0.075 | +++ | +++ | 0.25 | 0.25 | +++ | +++ | 0.075 | 0.5 | + | +++ |
| Control | | +++ | +++ | Control | | +++ | +++ | Control | | +++ | +++ |
| MIC: P = 0.5, S = 0.5 | | | | MIC: P = 1, S = 2.5 | | | | MIC: P = 0.5, S = 2.5 | | | |

TABLE III

| Primycin + Sisomicin | | | | | | | | | | | |
|---|---|---|---|---|---|---|---|---|---|---|---|
| *Bacillus cereus* CCM. 2010. | | | | *Vibrio parahaemolyticus* CCM. 5938. | | | | *Proteus vulgaris* CCM. 1799. | | | |
| P | S | Incubation | | P | S | Incubation | | P | S | Incubation | |
| µg/ml | µg/ml | $24^h$ | $48^h$ | µg/ml | µg/ml | $24^h$ | $48^h$ | µg/ml | µg/ml | $24^h$ | $48^h$ |
| 0.25 | 1 | 0 | 0 | 25 | 150 | 0 | 0 | 200 | 2.5 | 0 | 0 |
| 0.1 | 0.75 | 0 | 0 | 10 | 100 | 0 | 0 | 150 | 2.5 | 0 | 0 |
| 0.1 | 0.5 | 0 | 0 | 5 | 100 | 0 | 0 | 150 | 1 | 0 | 0 |
| 0.075 | 0.75 | 0 | 0 | 5 | 75 | 0 | 0 | 100 | 1 | 0 | 0 |
| 0.075 | 0.5 | 0 | 0 | 5 | 50 | 0 | 0 | 50 | 1 | 0 | 0 |
| 0.1 | 0.25 | ++ | +++ | 2.5 | 100 | 0 | 0 | 50 | 0.75 | 0 | 0 |
| 0.1 | 0.1 | +++ | +++ | 2.5 | 75 | 0 | 0 | 50 | 0.5 | 0 | + |
| 0.075 | 0.25 | +++ | +++ | 2.5 | 50 | 0 | 0 | 25 | 1 | + | ++ |
| 0.075 | 0.1 | +++ | +++ | 2.5 | 25 | ++ | ++ | 25 | 0.75 | + | ++ |
| 0.05 | 0.1 | +++ | +++ | 2.5 | 10 | ++ | ++ | 25 | 0.25 | +++ | +++ |
| Control | | +++ | +++ | Control | | +++ | +++ | Control | | +++ | +++ |
| MIC: P = 0.25, S = 1 | | | | MIC: P = 25, S = 150 | | | | MIC: P = >200, S = 2.5 | | | |

TABLE IV

| Primycin + Sisomicin | | | | | | | | | | | |
|---|---|---|---|---|---|---|---|---|---|---|---|
| *Salmonella Cholerae - suis* CCM. 5874. | | | | *Salmonella Cholerae - suis* subsp. Kunzendorf. CCM. 5967. | | | | *Escherichia coli* DSM. 30038 | | | |
| P | S | Incubation | | P | S | Incubation | | P | S | Incubation | |
| µg/ml | µg/ml | $24^h$ | $48^h$ | µg/ml | µg/ml | $24^h$ | $48^h$ | µg/ml | µg/ml | $24^h$ | $48^h$ |
| 75 | 2.5 | 0 | 0 | 200 | 2.5 | 0 | 0 | 200 | 2.5 | 0 | 0 |
| 50 | 1 | 0 | 0 | 150 | 2.5 | 0 | 0 | 150 | 2.5 | 0 | 0 |
| 50 | 0.75 | 0 | 0 | 100 | 1 | 0 | 0 | 150 | 1 | 0 | 0 |
| 25 | 1 | 0 | 0 | 50 | 1 | 0 | 0 | 100 | 1 | 0 | 0 |
| 25 | 0.75 | 0 | 0 | 50 | 0.75 | 0 | +++ | 50 | 1 | 0 | 0 |
| 10 | 1 | 0 | 0 | 50 | 0.5 | 0 | +++ | 50 | 0.75 | 0 | 0 |
| 25 | 0.5 | 0 | + | 25 | 1 | 0 | ± | 50 | 0.5 | 0 | 0 |
| 10 | 0.75 | 0 | ++ | 25 | 0.75 | 0 | +++ | 25 | 1 | ± | ± |
| 10 | 0.5 | 0 | ++ | 25 | 0.25 | +++ | +++ | 25 | 0.75 | ± | ± |
| 25 | 0.25 | +++ | +++ | | | | | 25 | 0.25 | +++ | +++ |
| Control | | +++ | +++ | Control | | +++ | +++ | Control | | +++ | +++ |
| MIC: P = 75, S = 2.5 | | | | MIC: P = 200, S = 2.5 | | | | MIC: P = 200, S = 2.5 | | | |

TABLE V

| Primycin + Doxycycline | | | | | | | | | | | |
|---|---|---|---|---|---|---|---|---|---|---|---|
| *Staphylococcus aureus* CCM. 885. | | | | *Staphylococcus aureus* CCM. 2326. | | | | *Staphylococcus aureus* CCM. 2514 | | | |
| P | D | Incubation | | P | D | Incubation | | P | D | Incubation | |
| µg/ml | µg/ml | $24^h$ | $48^h$ | µg/ml | µg/ml | $24^h$ | $48^h$ | µg/ml | µg/ml | $24^h$ | $48^h$ |
| 0.5 | 0.25 | 0 | 0 | 0.5 | 1 | 0 | 0 | 0.5 | 1 | 0 | 0 |
| 0.25 | 0.1 | 0 | 0 | 0.25 | 0.75 | 0 | 0 | 0.25 | 0.75 | 0 | 0 |
| 0.25 | 0.075 | 0 | 0 | 0.25 | 0.5 | 0 | 0 | 0.25 | 0.5 | 0 | 0 |
| 0.1 | 0.1 | 0 | 0 | 0.25 | 0.25 | 0 | 0 | 0.25 | 0.25 | 0 | 0 |
| 0.075 | 0.1 | 0 | 0 | 0.1 | 0.5 | 0 | 0 | 0.1 | 0.5 | 0 | 0 |
| 0.1 | 0.075 | 0 | ++ | 0.1 | 0.25 | 0 | 0 | 0.1 | 0.25 | 0 | 0 |
| 0.075 | 0.075 | 0 | +++ | 0.1 | 0.1 | 0 | 0 | 0.1 | 0.1 | 0 | 0 |
| 0.075 | 0.05 | 0 | +++ | 0.075 | 0.5 | 0 | 0 | 0.075 | 0.5 | 0 | 0 |
| 0.05 | 0.075 | ± | +++ | 0.075 | 0.1 | 0 | + | 0.075 | 0.1 | 0 | 0 |
| 0.05 | 0.05 | +++ | +++ | 0.05 | 0.05 | +++ | +++ | 0.05 | 0.05 | +++ | +++ |
| Control | | +++ | +++ | Control | | +++ | +++ | Control | | +++ | +++ |

TABLE V-continued

Primycin + Doxycycline

| Staphylococcus aureus CCM. 885. | | | | Staphylococcus aureus CCM. 2326. | | | | Staphylococcus aureus CCM. 2514 | | | |
|---|---|---|---|---|---|---|---|---|---|---|---|
| P μg/ml | D μg/ml | Incubation 24$^h$ | 48$^h$ | P μg/ml | D μg/ml | Incubation 24$^h$ | 48$^h$ | P μg/ml | D μg/ml | Incubation 24$^h$ | 48$^h$ |
| MIC: P = 0.5, D = 0.25 | | | | MIC: P = 0.5, D = 1 | | | | MIC: P = 0.5, D = 1 | | | |

TABLE VI

Primycin + Doxycycline

| Staphylococcus aureus DSM. 20231. | | | | Staphylococcus aureus CCM. 2515. | | | | Streptococcus agalactiae CCM. 5153. | | | |
|---|---|---|---|---|---|---|---|---|---|---|---|
| P μg/ml | D μg/ml | Incubation 24$^h$ | 48$^h$ | P μg/ml | D μg/ml | Incubation 24$^h$ | 48$^h$ | P μg/ml | D μg/ml | Incubation 24$^h$ | 48$^h$ |
| 0.5 | 0.5 | 0 | 0 | 0.25 | 0.25 | 0 | 0 | 0.5 | 0.5 | 0 | 0 |
| 0.25 | 0.25 | 0 | 0 | 0.1 | 0.1 | 0 | 0 | 0.25 | 0.25 | 0 | 0 |
| 0.1 | 0.25 | 0 | 0 | 0.1 | 0.075 | 0 | 0 | 0.1 | 0.25 | 0 | 0 |
| 0.075 | 0.25 | 0 | 0 | 0.075 | 0.1 | 0 | 0 | 0.075 | 0.25 | 0 | 0 |
| 0.1 | 0.1 | 0 | + | 0.075 | 0.075 | 0 | 0 | 0.1 | 0.1 | 0 | + |
| 0.075 | 0.1 | 0 | +++ | 0.075 | 0.05 | 0 | +++ | 0.075 | 0.1 | 0 | + |
| 0.075 | 0.075 | + | +++ | 0.05 | 0.1 | 0 | + | 0.075 | 0.075 | 0 | +++ |
| 0.05 | 0.1 | 0 | +++ | 0.05 | 0.075 | 0 | +++ | 0.05 | 0.075 | + | +++ |
| 0.05 | 0.075 | +++ | +++ | 0.05 | 0.05 | ± | +++ | 0.05 | 0.05 | ++ | +++ |
| | | | | 0.025 | 0.025 | +++ | +++ | 0.01 | 0.01 | +++ | +++ |
| Control | | +++ | +++ | Control | | +++ | +++ | Control | | +++ | +++ |
| MIC: P = 0.5, D = 0.5 | | | | MIC: P = 0.25, D = 0.25 | | | | MIC: P = 0.5, D = 0.5 | | | |

TABLE VII

Primycin + Doxycycline

| Bacillus cereus CCM. 2010. | | | | Listeria monocytogenes CCM. 5576. | | | | Salmonella cholerae - suis subsp. Kunzendorf. CCM. 5967. | | | |
|---|---|---|---|---|---|---|---|---|---|---|---|
| P μg/ml | D μg/ml | Incubation 24$^h$ | 48$^h$ | P μg/ml | D μg/ml | Incubation 24$^h$ | 48$^h$ | P μg/ml | D μg/ml | Incubation 24$^h$ | 48$^h$ |
| 0,25 | 1 | 0 | 0 | 0.25 | 0.25 | 0 | 0 | 200 | 2.5 | 0 | 0 |
| 0.1 | 0.75 | 0 | 0 | 0.1 | 0.1 | 0 | 0 | 150 | 1 | 0 | 0 |
| 0.1 | 0.5 | 0 | 0 | 0.1 | 0.075 | 0 | 0 | 100 | 1 | 0 | 0 |
| 0.1 | 0.25 | 0 | 0 | 0.075 | 0.1 | 0 | 0 | 100 | 0.75 | 0 | 0 |
| 0.075 | 0.75 | 0 | 0 | 0.075 | 0.075 | 0 | 0 | 50 | 1 | 0 | + |
| 0.075 | 0.5 | 0 | 0 | 0.075 | 0.05 | 0 | 0 | 50 | 0.75 | 0 | + |
| 0.05 | 0.5 | 0 | 0 | 0.05 | 0.1 | 0 | 0 | 50 | 0.5 | + | ++ |
| 0.075 | 0.25 | 0 | 0 | 0.05 | 0.075 | 0 | + | 25 | 1 | ± | ++ |
| 0.075 | 0.1 | 0 | ++ | 0.05 | 0.05 | 0 | + | 25 | 0.5 | +++ | +++ |
| 0.05 | 0.1 | ++ | +++ | 0.025 | 0.025 | +++ | +++ | 10 | 0.5 | +++ | +++ |
| Control | | +++ | +++ | Control | | +++ | +++ | Control | | +++ | +++ |
| MIC: P = 0.25, D = 1 | | | | MIC: P = 0.25, D = 0.25 | | | | MIC: P = 200, D = 2.5 | | | |

TABLE VIII

Primycin + Sisomicin + Doxycycline

| Staphylococcus aureus CCM. 2326. | | | | | Staphylococcus aureus CCM. 885. | | | | | Staphylococcus aureus CCM. 2515. | | | | |
|---|---|---|---|---|---|---|---|---|---|---|---|---|---|---|
| P μg./ml. | S μg./ml. | D μg./ml. | incubation 24$^h$ | 48$^h$ | P μg./ml. | S μg./ml. | D μg./ml. | incubation 24$^h$ | 48$^h$ | P μg./ml. | S μg./ml. | D μg./ml. | incubation 24$^h$ | 48$^h$ |
| 0.1 | 0.1 | 0.25 | 0 | 0 | 0.25 | 0.25 | 0.25 | 0 | 0 | 0.1 | 0.1 | 0.1 | 0 | 0 |
| 0.1 | 0.1 | 0.1 | 0 | 0 | 0.25 | 0.1 | 0.25 | 0 | 0 | 0.1 | 0.075 | 0.1 | 0 | 0 |
| 0.1 | 0.075 | 0.1 | 0 | 0 | 0.25 | 0.1 | 0.1 | 0 | 0 | 0.1 | 0.075 | 0.075 | 0 | 0 |
| 0.11 | 0.075 | 0.075 | 0 | 0 | 0.1 | 0.1 | 0.1 | 0 | 0 | 0.075 | 0.075 | 0.075 | 0 | 0 |
| 0.075 | 0.075 | 0.075 | 0 | 0 | 0.1 | 0.075 | 0.1 | 0 | 0 | 0.075 | 0.05 | 0.075 | 0 | 0 |
| 0.05 | 0.075 | 0.075 | 0 | 0 | 0.1 | 0.075 | 0.075 | 0 | 0 | 0.075 | 0.05 | 0.05 | 0 | 0 |
| 0.05 | 0.05 | 0.075 | 0 | 0 | 0.075 | 0.075 | 0.075 | 0 | +++ | 0.05 | 0.05 | 0.05 | 0 | 0 |
| 0.05 | 0.05 | 0.05 | 0 | 0 | 0.05 | 0.05 | 0.05 | ± | +++ | 0.025 | 0.05 | 0.05 | 0 | 0 |
| 0.025 | 0.025 | 0.025 | 0 | 0 | 0.05 | 0.05 | 0.025 | +++ | +++ | 0.025 | 0.025 | 0.05 | +++ | +++ |
| 0.01 | 0.025 | 0.025 | +++ | +++ | 0.05 | 0.025 | 0.025 | +++ | +++ | 0.025 | 0.025 | 0.025 | +++ | +++ |
| Control | | | +++ | +++ | Control | | | +++ | +++ | Control | | | +++ | +++ |
| MIC: P = 0.5, S = 0.5, D = 1. | | | | | MIC: P = 0.5, S = 0.25, D = 0.25 | | | | | MIC: P = 0.25, S = 0.25, D = 0.25 | | | | |

TABLE IX

Primycin + Sisomicin + Doxycycline

| Streptococcus agalactiae CCM. 5153 | | | | | Bacillus cereus CCM. 2010 | | | | | Listeria monocytogenes CCM. 5576 | | | | |
|---|---|---|---|---|---|---|---|---|---|---|---|---|---|---|
| P μg./ml. | S μg./ml. | D μg./ml. | Incubation 24ʰ | 48ʰ | P μg./ml. | S μg./ml. | D μg./ml. | Incubation 24ʰ | 48ʰ | P μg./ml. | S μg./ml. | D μg./ml. | Incubation 24ʰ | 48ʰ |
| 0.1 | 5 | 0.1 | 0 | 0 | 0.1 | 0.5 | 0.5 | 0 | 0 | 0.1 | 0.1 | 0.1 | 0 | 0 |
| 0.1 | 2.5 | 0.1 | 0 | 0 | 0.1 | 0.25 | 0.5 | 0 | 0 | 0.075 | 0.1 | 0.1 | 0 | 0 |
| 0.1 | 2.5 | 0.075 | 0 | 0 | 0.1 | 0.25 | 0.25 | 0 | 0 | 0.075 | 0.1 | 0.075 | 0 | 0 |
| 0.1 | 2.5 | 0.05 | 0 | 0 | 0.075 | 0.25 | 0.25 | 0 | 0 | 0.075 | 0.075 | 0.075 | 0 | 0 |
| 0.1 | 1 | 0.05 | 0 | 0 | 0.075 | 0.1 | 0.25 | 0 | 0 | 0.05 | 0.075 | 0.075 | 0 | 0 |
| 0.075 | 1 | 0.075 | 0 | 0 | 0.05 | 0.25 | 0.25 | 0 | 0 | 0.05 | 0.075 | 0.05 | 0 | 0 |
| 0.075 | 1 | 0.05 | 0 | 0 | 0.075 | 0.25 | 0.1 | 0 | +++ | 0.05 | 0.05 | 0.05 | 0 | 0 |
| 0.05 | 1 | 0.075 | 0 | 0 | 0.075 | 0.1 | 0.1 | 0 | +++ | 0.025 | 0.05 | 0.025 | 0 | 0 |
| 0.05 | 0.75 | 0.05 | 0 | 0 | 0.05 | 0.1 | 0.1 | 0 | +++ | 0.025 | 0.025 | 0.025 | 0 | +++ |
| 0.05 | 0.05 | 0.05 | ++ | +++ | 0.05 | 0.075 | 0.075 | ++ | +++ | 0.01 | 0.025 | 0.01 | + | +++ |
| Control | | | +++ | +++ | Control | | | +++ | +++ | Control | | | +++ | +++ |
| MIC: P = 0.5, S = 50, D = 0.5 | | | | | MIC: P = 0.25, S = 1, D = 1 | | | | | MIC: P = 0.25, S = 0.75, D = 0.25 | | | | |

TABLE X

Primycin + Sisomicin + Doxycycline

| Vibrio parahaemolyticus CCM. 5938 | | | | | Pseudomonas acidovorans CCM. 283 | | | | | Proteus mirabilis CCM. 1944 | | | | |
|---|---|---|---|---|---|---|---|---|---|---|---|---|---|---|
| P μg./ml. | S μg./ml. | D μg./ml. | Incubation 24ʰ | 48ʰ | P μg./ml. | S μg./ml. | D μg./ml. | Incubation 24ʰ | 48ʰ | P μg./ml. | S μg./ml. | D μg./ml. | Incubation 24ʰ | 48ʰ |
| 10 | 100 | 0.25 | 0 | 0 | 5 | 10 | 0.1 | 0 | 0 | 100 | 1 | 75 | 0 | 0 |
| 10 | 50 | 0.25 | 0 | 0 | 5 | 5 | 0.1 | 0 | 0 | 100 | 1 | 50 | 0 | 0 |
| 5 | 50 | 0.25 | 0 | 0 | 1 | 1 | 0.1 | 0 | 0 | 50 | 1 | 25 | 0 | 0 |
| 5 | 50 | 0.1 | 0 | 0 | 5 | 5 | 0.075 | 0 | 0 | 50 | 0.5 | 25 | 0 | 0 |
| 2.5 | 25 | 0.1 | 0 | 0 | 5 | 5 | 0.05 | 0 | 0 | 25 | 0.5 | 10 | 0 | 0 |
| 1 | 25 | 0.1 | 0 | 0 | 5 | 2.5 | 0.075 | 0 | 0 | 10 | 0.5 | 10 | 0 | 0 |
| 2.5 | 10 | 0.1 | + | ++ | 2.5 | 2.5 | 0.075 | 0 | 0 | 10 | 0.5 | 5 | 0 | +++ |
| 2.5 | 10 | 0.075 | ++ | ++ | 2.5 | 2.5 | 0.05 | 0 | 0 | 10 | 0.5 | 2.5 | 0 | +++ |
| 2.5 | 10 | 0.05 | ++ | ++ | 2.5 | 2.5 | 0.025 | 0 | 0 | 5 | 0.25 | 2.5 | +++ | +++ |
| 1 | 10 | 0.1 | + | ++ | 1 | 1 | 0.01 | ++ | +++ | 5 | 0.1 | 2.5 | +++ | +++ |
| | | | +++ | +++ | | | | +++ | +++ | | | | +++ | +++ |
| MIC: P = 25, S = 150, D = 0.5 | | | | | MIC: P = 50, S = 50, D = 0.5 | | | | | MIC: P = >200, S = 2.5, D = 150 | | | | |

TABLE XI

Primycin + Sisomicin + Doxycycline

| Shigella sonnei CCM. 1373 | | | | | Salmonella typhimurium CCM. 5445 | | | | | Salmonella cholerae - suis CCM. 5438 | | | | |
|---|---|---|---|---|---|---|---|---|---|---|---|---|---|---|
| P μg./ml. | S μg./ml. | D μg./ml. | Incubation 24ʰ | 48ʰ | P μg./ml. | S μg./ml. | D μg./ml. | Incubation 24ʰ | 48ʰ | P μg./ml. | S μg./ml. | D μg./ml. | Incubation 24ʰ | 48ʰ |
| 100 | 1 | 1 | 0 | 0 | 100 | 0.5 | 2.5 | 0 | 0 | 50 | 0.5 | 2.5 | 0 | 0 |
| 50 | 1 | 1 | 0 | 0 | 50 | 0.5 | 2.5 | 0 | 0 | 25 | 0.5 | 2.5 | 0 | 0 |
| 25 | 1 | 1 | 0 | 0 | 25 | 0.5 | 2.5 | 0 | 0 | 25 | 0.25 | 1 | 0 | 0 |
| 10 | 0.5 | 1 | 0 | 0 | 25 | 0.25 | 2.5 | 0 | 0 | 10 | 0.25 | 1 | 0 | 0 |
| 10 | 0.5 | 0.5 | 0 | 0 | 10 | 0.1 | 1 | 0 | 0 | 5 | 0.25 | 1 | 0 | 0 |
| 10 | 0.5 | 0.25 | 0 | 0 | 5 | 0.1 | 2.5 | 0 | 0 | 5 | 0.1 | 1 | 0 | 0 |
| 5 | 0.5 | 0.5 | 0 | 0 | 10 | 0.075 | 2.5 | 0 | +++ | 1 | 0.1 | 1 | 0 | 0 |
| 5 | 0.25 | 0.5 | 0 | 0 | 5 | 0.075 | 2.5 | 0 | +++ | 2.5 | 0.1 | 0.75 | 0 | 0 |
| 5 | 0.1 | 0.5 | 0 | +++ | 10 | 0.075 | 1 | +++ | +++ | 2.5 | 0.075 | 0.5 | ++ | +++ |
| 5 | 0.1 | 0.25 | +++ | +++ | 10 | 0.1 | 1 | +++ | +++ | 2.5 | 0.05 | 0.5 | +++ | +++ |
| Control | | | +++ | +++ | Control | | | +++ | +++ | Control | | | +++ | +++ |
| MIC: P = 150, S = 2.5, D = 2.5 | | | | | MIC: P = 150, S = 0.75, D = 5 | | | | | MIC: P = 75, S = 0.75, D = 5 | | | | |

TABLE XII

Primycin + Sisomicin + Doxycycline

| Salmonella cholera - suis CCM. 5874 | | | | | Salmonella cholerae - suis subsq. Kunzendorf CCM. 5967 | | | | | Escherichia coli DSM 30038 | | | | |
|---|---|---|---|---|---|---|---|---|---|---|---|---|---|---|
| P μg./ml. | S μg./ml. | D μg./ml. | Incubation 24ʰ | 48ʰ | P μg./ml. | S μg./ml. | D μg./ml. | Incubation 24ʰ | 48ʰ | P μg./ml. | S μg./ml. | D μg./ml. | Incubation 24ʰ | 48ʰ |
| 50 | 1 | 2.5 | 0 | 0 | 100 | 1 | 1 | 0 | 0 | 25 | 0.5 | 1 | 0 | 0 |
| 25 | 1 | 2.5 | 0 | 0 | 50 | 1 | 1 | 0 | 0 | 10 | 0.5 | 1 | 0 | 0 |
| 10 | 1 | 2.5 | 0 | 0 | 25 | 1 | 1 | 0 | 0 | 10 | 0.25 | 1 | 0 | 0 |
| 5 | 0.5 | 1 | 0 | 00 | 25 | 0.5 | 0.5 | 0 | 0 | 10 | 0.5 | 0.75 | 0 | 0 |
| 5 | 0.5 | 0.75 | 0 | 0 | 10 | 0.5 | 0.5 | 0 | 0 | 10 | 0.25 | 0.75 | 0 | 0 |

TABLE XII-continued

Primycin + Sisomicin + Doxycycline

| Salmonella cholera - suis CCM. 5874 | | | | | Salmonella cholerae - suis subsq. Kunzendorf CCM. 5967 | | | | | Escherichia coli DSM 30038 | | | | |
|---|---|---|---|---|---|---|---|---|---|---|---|---|---|---|
| P µg./ml. | S µg./ml. | D µg./ml. | Incubation 24$^h$ | 48$^h$ | P µg./ml. | S µg./ml. | D µg./ml. | Incubation 24$^h$ | 48$^h$ | P µg./ml. | S µg./ml. | D µg./ml. | Incubation 24$^h$ | 48$^h$ |
| 5 | 0.5 | 0.5 | 0 | 0 | 10 | 0.25 | 0.5 | 0 | 0 | 10 | 0.5 | 0.5 | 0 | 0 |
| 2.5 | 0.5 | 0.75 | 0 | +++ | 10 | 0.5 | 0.25 | 0 | 0 | 5 | 0.5 | 0.5 | 0 | 0 |
| 2.5 | 0.5 | 0.5 | 0 | +++ | 5 | 0.5 | 0.5 | 0 | 0 | 5 | 0.25 | 0.25 | + | +++ |
| 2.5 | 0.25 | 0.5 | +++ | +++ | 5 | 0.25 | 0.25 | 0 | +++ | 2.5 | 0.25 | 0.25 | + | +++ |
| 2.5 | 0.25 | 0.25 | +++ | +++ | 5 | 0.1 | 0.1 | +++ | +++ | 1 | 0.25 | 0.25 | +++ | +++ |
| Control | | | +++ | +++ | Control | | | +++ | +++ | Control | | | +++ | +++ |
| MIC: P = 75, S = 2.5, D = 5 | | | | | MIC: P = 200, S = 2.5, D = 2.5 | | | | | MIC: P = 200, S = 2.5, D = 5 | | | | |

TABLE XIII

Primycin + Sisomicin + Doxycycline

| Escherichia coli ATCC. 11775 | | | | | Escherichia coli CCM. 180 | | | | | Serratia Macrescens CCM. 303 | | | | |
|---|---|---|---|---|---|---|---|---|---|---|---|---|---|---|
| P µg./ml. | S µg./ml. | D µg./ml. | Incubation 24$^h$ | 48$^h$ | P µg./ml. | S µg./ml. | D µg./ml. | Incubation 24$^h$ | 48$^h$ | P µg./ml. | S µg./ml. | D µg./ml. | Incubation 24$^h$ | 48$^h$ |
| 25 | 0.5 | 2.5 | 0 | 0 | 10 | 0.25 | 1 | 0 | 0 | 100 | 5 | 10 | 0 | 0 |
| 10 | 0.5 | 2.5 | 0 | 0 | 5 | 0.25 | 1 | 0 | 0 | 50 | 5 | 10 | 0 | 0 |
| 10 | 0.5 | 1 | 0 | 0 | 5 | 0.1 | 1 | 0 | 0 | 25 | 5 | 10 | 0 | 0 |
| 10 | 0.25 | 1 | 0 | 0 | 5 | 0.1 | 0.75 | 0 | 0 | 25 | 2.5 | 10 | 0 | 0 |
| 5 | 0.5 | 1 | 0 | 0 | 2.5 | 0.1 | 1 | 0 | 0 | 10 | 2.5 | 10 | 0 | 0 |
| 5 | 0.25 | 1 | 0 | 0 | 2.5 | 0.1 | 0.75 | 0 | 0 | 10 | 2.5 | 5 | 0 | 0 |
| 5 | 0.25 | 0.75 | 0 | 0 | 2.5 | 0.1 | 0.5 | 0 | 0 | 5 | 2.5 | 5 | 0 | + |
| 1 | 0.25 | 0.5 | 0 | + | 1 | 0.1 | 0.75 | 0 | 0 | 5 | 1 | 5 | 0 | ++ |
| 1 | 0.1 | 0.5 | 0 | +++ | 1 | 0.075 | 0.75 | 0 | 0 | 5 | 1 | 2.5 | + | +++ |
| 1 | 0.05 | 0.1 | +++ | +++ | 1 | 0.05 | 0.5 | +++ | +++ | 5 | 0.75 | 2.5 | +++ | +++ |
| Control | | | +++ | +++ | Control | | | +++ | +++ | Control | | | +++ | +++ |
| MIC: P = > 200, S = 1, D = 5 | | | | | MIC: P = 200, S = 0.75, D = 2.5 | | | | | MIC: P = 200, S = 10, D = 25 | | | | |

Further details of the invention are illustrated by the following Examples which serve merely for illustration and not for limitation.

EXAMPLES

1. I. Composition of a powder ampoule

| | |
   |---|---|
   | Sisomicin | 0.10 g. |
   | Doxycycline.HCl | 0.10 g. |
   | Sodium acetate | 0.533 g. |

II. Composition of a solvent ampoule:

| | |
   |---|---|
   | Primycin heterocolloid (active ingredient content: 0.1 g.) | 10.0 g. |
   | cetyl trimethyl ammonium bromide | 0.5 mg. |

The composition is prepared as follows:

Sisomicin, doxycycline and previously pulverized sodium acetate are homogenized, measured into a powder ampoule and sealed (I). Cetyl trimethyl ammonium bromide is dissolved in heterocolloidal primycin and filled into 10 ml. ampoules and sealed (II). Prior to use the content of the solvent ampoule is injected to a powder ampoule and after dissolution it is pressed into the udders with a plastic needle. The thus prepared composition may be finished by methods known per se into a two-chamber syringe.

2. 
   | | |
   |---|---|
   | Sisomicin | 0.10 g. |
   | Doxycycline.HCl | 0.10 g. |
   | Primycin-heterocolloidal (active ingredient content: 0.1 g.) | 10.00 g. |
   | Sodium acetate | 0.97 g. |
   | cetyl-trimethyl-ammonium-bromide | 0.5 mg. |

The composition is prepared as follows:

Sodium acetate is dissolved in primycin-heterocolloid, filled into powder ampoules and lyophilized conventionally, Sisomicin and doxycycline are added to the lyophilized product in dried state and the powder ampoule is sealed with a rubber stopper as usually. The content of the powder ampoule is dissolved prior to use in 10 ml. of distilled water and pressed into the udders with a plastic needle or by other methods.

3. 
   | | |
   |---|---|
   | Primycin-heterocolloid (alcoholic) (active ingredient content: 0.1 g.) | 10.00 g. |
   | Castor-oil | 10.00 g. |
   | Cholesterol | 0.25 g. |
   | Sisomicin | 0.10 g. |
   | Doxycycline.HCl | 0.10 g. |

The composition is prepared as follows:

Alcoholic solution of primycin-heterocolloid is mixed with caster-oil and the alcohol is distilled off, preferably in vacuo. Cholesterol is dissolved, preferably hot in the caster oil-primycin mixture. The dried sisomicin and doxycycine are suspended conventionally in the cooled mixture of caster oil and primycin.

The suspension thus obtained is filled into suitable plastic ampoules or an aluminum tube and equipped with a plastic needle most suitable for use.

4. I. Composition of a powder ampoule

| | |
   |---|---|
   | Sisomicin | 0.10 g. |

-continued

|  | |
|---|---|
| Doxycycline.HCl | 0.10 g. |
| II. Composition of a solvent ampoule | |
| Primycin | 10.0 g. |
| (active ingredient content: 0.1 g.) | |
| cetyl-trimethyl-ammonium-bromide | 0.5 g. |
| disodium hydrogen phosphate | 0.1716 g. |
| citric acid cryst | 0.7596 g. |

The composition is prepared as follows:

Doxycycline and sisomicin are mixed together and sealed into an ampoule (I). Cetyl-trimethyl-ammonium bromide, crystalline disodium hydrogen phosphate ($Na_2HPO_4.12H_2O$) and citric acid are dissolved in primycine-heterocolloid ($C_6H_8O_7.H_2O$), filled to ampoules and sealed (II).

| 5. Ointment | |
|---|---|
| Sisomicin | 0.10 g. |
| Doxycycline.HCl | 0.10 g. |
| Primycin | 0.10 g. |
| Polyethyleneglycol 400 | 4.85 g. |
| Polyethyleneglycol 4000 | 4.85 g. |

The composition is prepared as follows:

Sisomicin, doxycycline and primycin pulverized under 50μ are used for the preparation of the ointment. Polyethyleneglycol 400 and polyethylene 4000 are homogenized and the active ingredients are mixed with a small part of the homogenized excipients and gradually mixed with the rest of the excipients. The mixture is then filled into tubes.

| 6. Aerosol filmformer | |
|---|---|
| Sisomicin | 0.10 g. |
| Doxycycline.HCl | 0.10 g. |
| Primycin | 0.10 g. |
| Polyvinylpyrrolidone | 2.0 g. |
| Anhydrous ethanol | 47.7 g. |
| Freon 11/12 5050 | 50.0 g. |

The composition is prepared as follows:

The dried and pulverized (under 50μ) Sisomicin, Doxycycline.HCl and Primycin are introduced into aerosol bottles whereafter the anhydrous ethanolic polyvinylpyrrolidone solution is added. The bottles are filled and sealed by methods known per se.

| 7. Aerosol talc | |
|---|---|
| Sisomicin | 0.10 g. |
| Doxycycline.HCl | 0.10 g. |
| Primycin | 0.10 g. |
| Isopropylmyristate | 1.0 g. |
| Freon 11/12 5050 | 98.7 g. |

The composition is prepared as follows:

The previously dried and pulverized (under 50μ) sisomicin, doxycycline.HCl and primycin are homogenized and triturated with isopropylmyristate. Each dose is filled into aerosol bottles. The bottles are filled and sealed by method known per se.

8. Comparative tests carried out with primycin and primycin-combination on patients suffering from mastitis Primycin and primycin combination are examined on clinically manifested patients suffering from mastitis. The tests were carried out by thermographic method (cholesteric film set).

As reference substances active ingredients commercially available in Hungary, such as Neomaticur, Mastalone were employed.

Distribution of diseases:
 simple catarrhal mastitis
 acute contagious catarrhal mastitis
 cronic contagious catarrhal mastitis
 purulent mastitis with abscesses Treatment:
 1. Primycin 100 mg./udder quarter
  8 recovered out of 15 cases
 2. Primycin-combination

| Composition: | I. powder ampoule | |
|---|---|---|
| | sisomicin (dried) | 85 mg. |
| | doxycycline (dried) | 100 mg. |
| | sodium acetate (anhydrous) | 533 mg. |
| | prednisolone | 10 mg. |
| | II. solvent ampoule | |
| | primycin heterocolloid (active ingredient content: 0.1 g.) | 20 ml. |
| | cetyl trimethyl-ammoniumbromide | 1.0 mg. |

The primycin combination proved to be effective in 14 cases out of 16 cases. In the remaining one case the animal had to be sacrified due to abscess-formation while the other case was a chronic contagious catarrhal mastitis.

The above results are confirmed by in vitro test-results.

We claim:

1. A synergistic antibacterial composition which consists essentially of a synergistic combination of pharmaceutically effective amounts of primycin or a pharmaceutically acceptable acid addition salt thereof in the range of 5 to 50% by weight and of sisomicin or a pharmaceutically acceptable acid addition salt thereof in the range of 95 to 50% by weight.

2. The synergistic antibacterial composition defined in claim 1 wherein the pharmaceutically acceptable acid addition salt of the primycin is primycin sulfate and the pharmaceutically acceptable acid addition salt of the sisomicin is sisomicin sulfate.

* * * * *